US007043304B1

(12) United States Patent
Griffith et al.

(10) Patent No.: US 7,043,304 B1
(45) Date of Patent: May 9, 2006

(54) METHOD OF CONTROLLING AN IMPLANTABLE NEURAL STIMULATOR

(75) Inventors: Glen A. Griffith, Newbury Park, CA (US); Michael A. Faltys, Northridge, CA (US)

(73) Assignee: Advanced Bionics Corporation, Valencia, CA (US)

( * ) Notice: Subject to any disclaimer, the term of this patent is extended or adjusted under 35 U.S.C. 154(b) by 0 days.

(21) Appl. No.: 10/999,748

(22) Filed: Nov. 30, 2004

Related U.S. Application Data

(62) Division of application No. 09/981,252, filed on Oct. 16, 2001, now Pat. No. 6,842,647.

(60) Provisional application No. 60/242,336, filed on Oct. 20, 2000.

(51) Int. Cl.
*A61N 1/32* (2006.01)

(52) U.S. Cl. .......................................... 607/57; 607/60

(58) Field of Classification Search ................. 600/25; 607/57, 60, 32, 31; 604/890.1; 128/903
See application file for complete search history.

(56) References Cited

U.S. PATENT DOCUMENTS 4,189,713 A 2/1980 Duffy
4,790,019 A 12/1988 Hueber
4,845,755 A 7/1989 Busch et al.
4,918,736 A 4/1990 Bordewijk
5,024,224 A * 6/1991 Engebretson ................ 607/57
5,083,312 A 1/1992 Newton et al.
5,603,726 A 2/1997 Schulman et al.
6,067,474 A 5/2000 Schulman et al.
6,247,474 B1 6/2001 Greeninger et al.
6,272,382 B1 8/2001 Faltys et al.
6,308,101 B1 10/2001 Faltys et al.

FOREIGN PATENT DOCUMENTS

WO WO-97/01314 A1 1/1997

* cited by examiner

*Primary Examiner*—Mark Bockelman
(74) *Attorney, Agent, or Firm*—Bryant R. Gold; Victoria A. Poissant

(57) ABSTRACT

A method of controlling an implantable neural stimulation system, such as an auditory Fully Implantable System (FIS), uses a first signal path to send signals to the implant device, and a second signal path to receive signals from the implant device. The combination of these two signal paths provides a full-duplex channel between the remote control unit and the implant device through which appropriate control and status signals may be sent and received. In one embodiment, the first signal path comprises an audio signal path through which audio control signals, e.g., a tone sequence or a 32-bit word FSK modulated between 300 and 1200 Hz, are sent; and the second signal path comprises a RF signal path through which a BPSK, QPSK or FM modulated RF signal is received. The full-duplex channel allows operation of the remote control unit, i.e., allows signals to be successfully sent to and received from the implant device, from as far away as 45–60 cm from the implant device.

12 Claims, 3 Drawing Sheets

METHOD OF CONTROLLING AN IMPLANTABLE NEURAL STIMULATOR

The present application is a Divisional of U.S. application Ser. No. 09/981,252, filed Oct. 16, 2001 now U.S. Pat. No. 6,842,647, which claims the benefit of U.S. Provisional Application Ser. No. 60/242,336, filed Oct. 20, 2000, which applications are incorporated herein by reference.

BACKGROUND OF THE INVENTION

The present disclosure relates to implantable medical devices and systems, and more particularly to a implantable neural stimulation system and an external remote control unit used to control and monitor the implantable neural stimulation system. In a preferred embodiment, the implantable neural stimulation system comprises an auditory fully implantable system (FIS) adapted to provide selective electrical stimulation to the auditory nerve through electrodes implanted in the cochlea.

An auditory Fully Implantable System (FIS) is intended to be fully operational during normal use without the need for any external components. However, such FIS still requires an external control device in order to adjust various parameters of operation, such as stimulation intensity. Since there are no external controls provided with an FIS, there is a need for an external remote control device, or a remote control unit, to allow the various parameters of operation of the FIS to be controlled.

It is known in the art to use an acoustic remote control unit with a hearing aid system, including a hearing aid system that is at least partially implanted. See, e.g., international PCT publication WO97/01314, published on Jan. 16, 1997.

In U.S. Pat. No. 4,189,713, entitled "Remote Control Systems", there is disclosed an acoustic remote control link wherein different value bits are transmitted as pulses containing different number of carrier cycles. Pulse-counting circuitry is then employed within the receiver to identify the received bits as either a "1" of a "0" on the basis of the received pulses containing numbers of carrier cycles in one or other of two ranges.

In U.S. Pat. No. 4,790,019, entitled "Remote Hearing Aid Volume Control", a small hearing aid is disclosed, e.g., of the type worn behind the ear or even in the ear or the ear canal. Also disclosed is a remote sound wave control signal emitter that emits sound wave control signals within the range of the hearing aid microphone input. The control signals are used for the purpose of adjusting the volume/sensitivity of the hearing aid. Frequency selective circuitry is utilized inside the hearing aid to separate control signal components from normal to-be-heard signal components. A frequency shift keying (FSK) type of modulation is suggested as one type of modulation for the control signal. In one embodiment, the control signal emitter emits a carrier frequency outside of the receiving range of the hearing aid earphone, preferably above the receiving range of the earphone, thereby rendering the control signals inaudible to the hearing aid user.

In U.S. Pat. No. 4,845,755, entitled "Remote Control Hearing Aid", there is taught a hearing aid with a wireless remote control in which the microphone of the hearing aid is used as the receiving element for the control signals. The wideband nature of the miniature microphone is relied upon to sense incoming control signals that are imperceptible to the human ear, e.g., signals in the ultrasonic range up to 25 KHz, or signals that utilize resonance properties of the microphone between 45 KHz and 59 KHz.

In U.S. Pat. No. 4,918,736, entitled "Remote Control System For Hearing Aids", the combination of a hearing aid adapted to be supported upon the head of a user and a remote control unit is shown. The remote control unit provides control of an operational parameter of the hearing aid, such as the amplification factor, so that the hearing aid can remain rather small and occupy a smaller amount of space. The wireless transmission of the control signal from the remote control unit is by means of acoustic waves. The microphone of the hearing aid functions as the pick-up for receiving the control signal from the remote control unit. The control signal lies in a frequency region which is outside of the operating range of the electro-acoustic transducer of the hearing aid, but still within the frequency range of the microphone. The control signal is used to switch the hearing aid on or off, change volume, frequency settings or other operational parameters, without disturbing the user of the hearing aid. The acoustic control signal may be modulated, e.g., with AM, FM, or DTMF modulation.

Additionally, in U.S. Pat. No. 5,083,312, entitled "Programmable Multichannel Hearing Aid with Adaptive Filter", there is taught a small hearing aid device, preferably an in-the-canal hearing aid, that may be conveniently and inexpensively programmed with remotely generated audible signals. The preferred audio programming signal disclosed in the '312 patents consists of dual-tone multiple-frequency (DTMF) tones. One of the stated advantages of using DTMF tones is that clinicians can reprogram the hearing aid on site or over the telephone. Further, by using a unique command sequence as the programming signal, the possibility of inadvertent programming due to ordinary speaking or other environmental sound patterns, is greatly minimized.

Thus, it is seen, that remotely-generated acoustic signals have long been used to program or control a hearing aid device or system. However, none of the teachings of the prior art specifically address how to program or control a fully implantable system (FIS).

SUMMARY OF THE INVENTION

The present disclosure addresses the above and other needs by providing an implantable neural stimulation system, such as an auditory fully implantable system (FIS), that includes: (1) an implanted device capable of providing desired tissue or nerve stimulation; and (2) a remote control device that controls the implant device by, e.g., selectively adjusting certain stimulation parameters associated with the tissue stimulation provided by the implanted device.

The remote control unit used with the neural stimulation system of the present disclosure advantageously uses a first signal path to send signals to the implant device, and a second signal path to receive signals from the implant device. The combination of these two signal paths advantageously provides a full-duplex channel between the remote control unit and the implant device through which appropriate control and status signals may be sent and received. When a control signal is sent to the implant device, it is thus possible for the implant device to signal that such control signal has been successfully received, thereby assuring the reliable transfer of control signals to the implant device.

In a preferred embodiment, such full-duplex channel allows operation of the remote control unit, i.e., allows signals to be successfully sent to and received from the implant device, from as far away as 45–60 cm (~18–24 inches) from the implant device.

In accordance with one aspect of the present disclosure, the first signal path, i.e., the signal path through which the remote control unit sends control signals to the implant device comprises an audio tone generator that generates a select sequence of audio tones, or other acoustic control signal, which audio tones or acoustic signal are sensed by the microphone associated with the implant device. The acoustic control signal, in one embodiment, comprises a n-bit burst control signal, where n is an integer between 4 and 32, modulated with FSK modulation that varies between frequency f1 and frequency f2. While the values of n, f1 and f2 may assume any suitable values, in one preferred embodiment, n is 32, f1 is 1200 Hz and f2 is 2400 Hz.

In accordance with another aspect of the present disclosure, the second signal path, i.e., the signal path through which the remote control unit receives signals from the implant device, uses the induction coil already present within the FIS as a broadcast antenna. The FIS includes a back telemetry transmitter that broadcasts an appropriate modulated RF signal, e.g., a 10.7 MHz BPSK (binary phase-shift key) modulated signal, or a frequency-modulated (FM) signal, back to the remote control unit. The remote control unit includes a rod antenna to receive the back telemetry signal as well as special reception circuitry configured to be highly sensitive to the back telemetry signal.

In accordance with yet another aspect of the present disclosure, the remote control unit includes a display panel, screen or other visual indicator device through which messages, symbols, status indications, or icons may be displayed which acknowledge the acceptable reception of data, or signals from the implant device, as well as provide other status information.

BRIEF DESCRIPTION OF THE DRAWINGS

The above and other aspects, features and advantages of the present disclosure will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
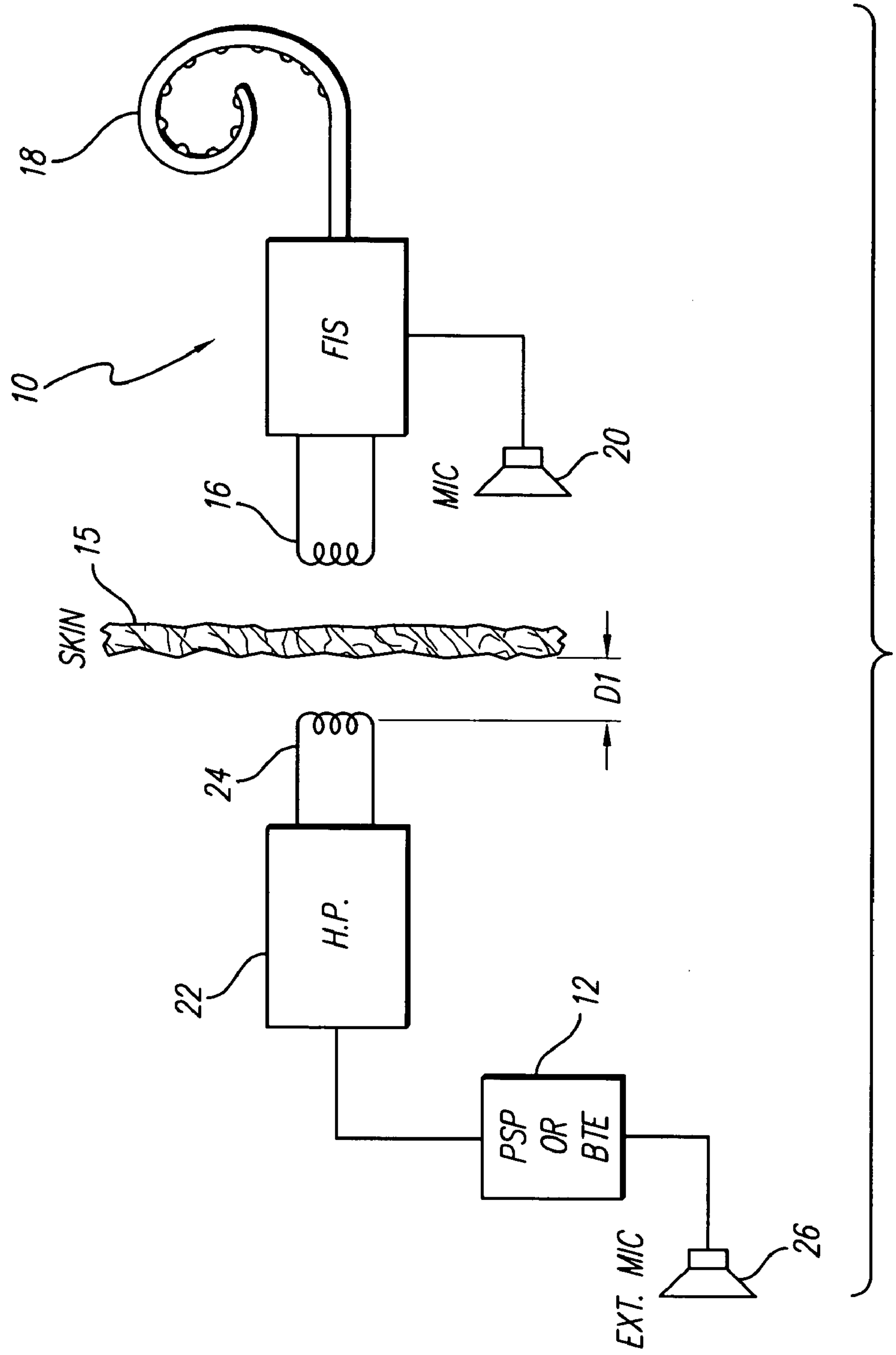
FIG. 1 illustrates a block diagram of a fully implantable system (FIS) designed to provide electrical stimulation to the cochlea of a user in order to assist the user to hear, and more particularly shows operation of such an FIS as augmented through the use of an external pocket speech processor (PSP) or behind-the-ear (BTE) unit having an external coil located a distance D1 from an implanted coil associated with the FIS.

The following description is of the best mode presently contemplated for carrying out the invention. This description is not to be taken in a limiting sense, but is made merely for the purpose of describing the general principles of the invention. The scope of the invention should be determined with reference to the claims.

The present disclosure, in accordance with one embodiment thereof, is directed to a neural stimulation system. Such neural stimulation system includes an implantable neural stimulator and a remote control unit. The implantable neural stimulator, which may be, e.g., an auditory fully implantable system, comprises: (a) an electrode array having a multiplicity of electrode contacts positionable to be in contact with body tissue that is to be stimulated; (b) an implantable coil; (c) an implantable microphone (any device capable of sensing externally-generated acoustic signals); and (d) implantable control circuitry connected to the electrode array, implantable coil, and implantable microphone. The implantable control circuitry typically includes: (i) pulse generation circuitry that generates stimulation pulses that are applied to the body tissue through selected ones of the multiplicity of electrode contacts as controlled by audio control signals received through the implantable microphone, and (ii) a transmitter circuit that generates a back telemetry signal and applies the back telemetry signal to the implanted coil for broadcasting to the remote control unit. The remote control unit typically comprises: (a) an external coil; (b) a receiver circuit connected to the external coil that senses the back telemetry signal broadcast from the implantable control circuitry through the implantable coil; (c) a speaker (any device capable of emitting or broadcasting an audio signal, such as a series or sequence of audio tones); and (d) an audio transmitter coupled to the speaker that defines the audio control signals that are broadcast or emitted from the speaker.

In operation, the audio control signals are sent to the implantable neural stimulator from the remote control unit for the purpose of controlling the implantable neural stimulator, and the back telemetry signals generated by the implanted neural stimulator are sent to the remote control unit for the purpose of verifying receipt of control signals and for providing status information regarding operation of the implantable control unit. Such verification/status information typically includes an indication as to whether audio control signals sent to the implantable neural stimulator were successfully received within the implantable neural stimulator, and may include other status information, e.g., the status of the battery, or other power source, included within the implantable neural stimulator, the settings of the stimulus parameters (amplitude, pulse width, frequency, etc.) stored in the implantable neural stimulator, and the like.

In accordance with another embodiment, the present disclosure is directed to a remote control unit adapted to control an implantable neural stimulator. Such implantable neural stimulator has an implantable microphone, or equivalent, adapted to sense an externally-generated acoustic control signal, and an rf transmitter adapted to generate a RF (radio frequency) back telemetry signal. The remote control unit comprises: (a) an acoustic generator that generates acoustic control signals; and (b) an RF receiver circuit adapted to receive RF back telemetry signals generated by the implantable neural stimulator. The acoustic generator has the capacity to send acoustic control signals to the implantable neural stimulator over a distance of at least about 45 cm, and preferably over a distance of at least about 60 cm, and the receiver circuit has the sensitivity to receive RF back telemetry signals from the implantable neural stimulator over the same distances.

The description of the disclosure that follows is directed to an auditory fully implantable system (FIS) designed to provide electrical stimulation to the cochlea of a user in order to assist the user to hear. It is to be understood, however, that the disclosure is not limited to use with an auditory FIS, but may be used with any fully implantable system that includes an implant device, e.g., an implantable stimulator and/or sensor, that requires control or monitoring, from time to time, through the use of an external (non-implanted) remote control unit.

Turning first to FIG. 1, there is shown a block diagram of a fully implantable system (FIS) 10 designed to provide electrical stimulation to the cochlea of a user in order to assist the user to hear. More particularly, FIG. 1 shows operation of such an FIS 10 as augmented through the use of an external pocket speech processor (PSP) or behind-the-ear (BTE) unit 12 having an external coil 24 located a distance D1 from the skin surface 15 of the user. In typical applications, the distance D1 is between 0-to-8 mm. The FIS 10 is coupled to an implant coil 16, an implanted microphone 20, and a cochlear electrode array 18. The PSP or BTE 12 is coupled to the FIS 10 through a headpiece 22 and an external coil 24. An external microphone 26 is connected to the PSP or BTE 12.

When used as illustrated in FIG. 1, i.e., when the FIS 10 is augmented through the use of a PSP or BTE 12, audio signals are sensed by the external microphone 26 and are processed by speech processing circuitry contained within the PSP/BTE 12. Such processing produces stimulation control signals which are coupled into the FIS through an inductive link created between the external coil 24 and the implant coil 16. Typically, power is also coupled into the FIS 10 through this same link. That is, the PSP/BTE generates a suitable RF carrier signal. This RF carrier signal is modulated with the stimulation control signals. The modulated RF carrier signal is coupled into the FIS 10 through the inductive link between external coil 24 and internal coil 16. Rectification circuitry and demodulation circuitry within the FIS 10 extract the power and stimulation control signals, respectively, for use by the FIS, in conventional manner. In response to the stimulation control signals, the FIS 10 generates appropriate stimulation pulses that are applied to selected electrodes included within the electrode array. These stimulation pulses are sensed by nerves within the cochlea, and provide the user of the system with the sensation of hearing.

A more complete description of the operation and construction of the FIS 10, including its use and operation when augmented with the PSP/BTE 12, may be found in U.S. Pat. Nos. 6,067,474 and 6,272,382, incorporated herein by reference; or in applicant Falty's application Ser. No. 09/404,966, filed Sep. 24, 1999, now issued as U.S. Pat. No. 6,308,101, which patent is assigned to the same assignee as is the present application and is likewise incorporated herein by reference.

Figure 2:
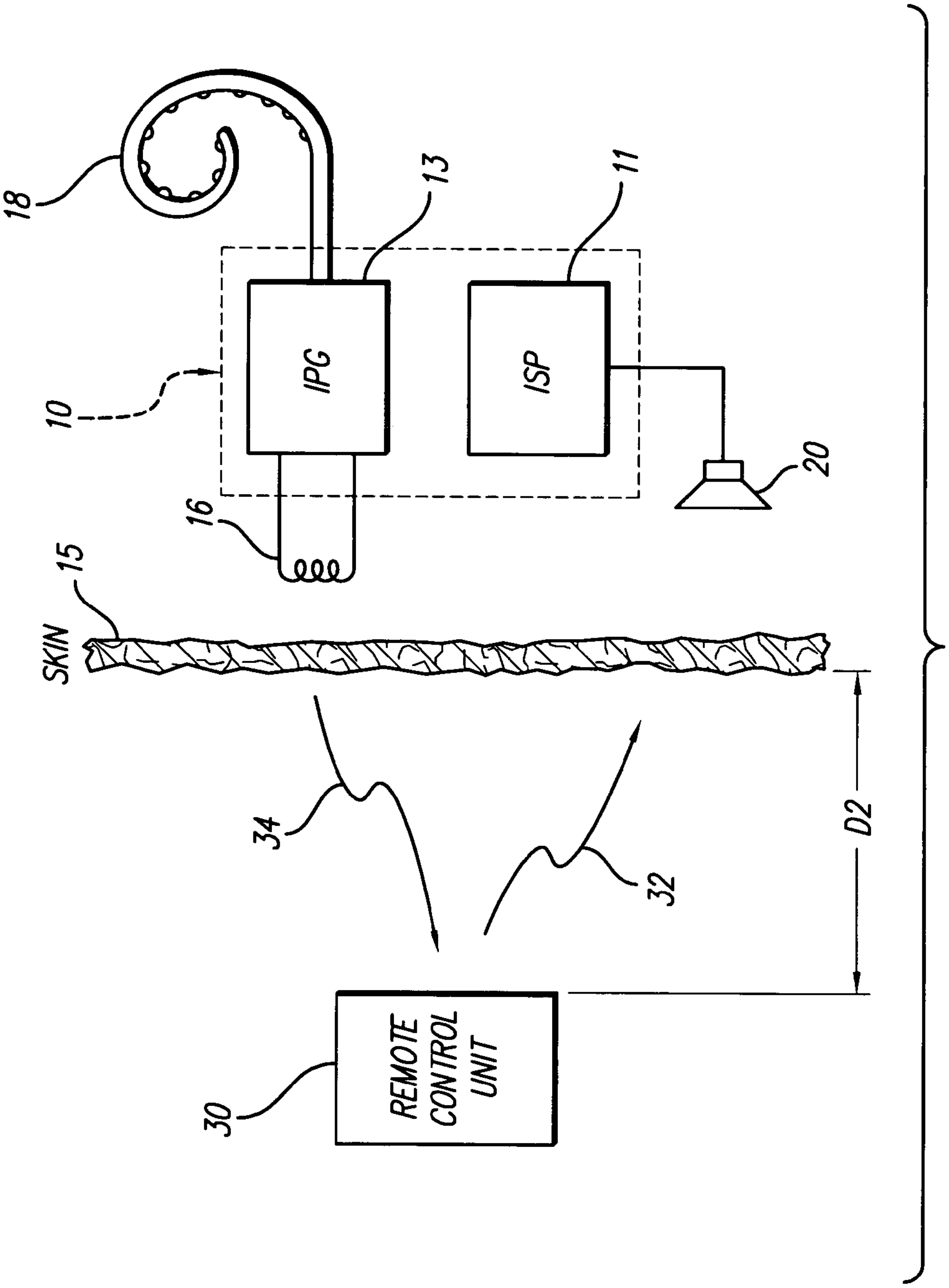
FIG. 2 is a block diagram that illustrates further detail of the FIS of FIG. 1, and depicts the manner in which a remote control unit made in accordance with the present disclosure may be used to control and monitor the operation of the FIS from a distance D2 from the FIS, where D2 is much greater than D1.

Turning next to FIG. 2, a block diagram is shown that illustrates further detail of the FIS 10 of FIG. 1. More particularly, FIG. 2 depicts the manner in which a remote control unit (RCU) 30 made in accordance with the present disclosure may be used to control and monitor the operation of the FIS from a distance D2 from the skin surface 15 of the user. The distance D2 is usually much greater than the distance D1 (the distance between the external coil 24 of the HP 22 and skin surface 15, illustrated in FIG. 1). Typically, the distance D2 is on the order of 45–60 cm. FIG. 2 further illustrates that the FIS 10 may include two subsystems: an implantable pulse generator (IPG) 13, and an implantable speech processor (ISP) 11.

As taught in the above-referenced '474 and/or '382 patents, and/or the '101 patent, the IPG 13 and the ISP 11 may be housed in separate implantable housings or cases, which housings or cases are in turn electrically coupled to each other, e.g., through hard wire cables/connectors, or through inductive/RF coupling loops. Alternatively, the IPS circuits and the IPG circuits may be housed within the same implantable housing. The manner in which the ISP circuits 11 and the IPG circuits 13 are arranged and/or configured within the FIS 10 is not important for purposes of the present disclosure. All that is important for purposes of the present disclosure is that the FIS 10 circuitry include back telemetry circuitry coupled to the implant coil 16 through which a back telemetry signal may be transmitted, and an implanted microphone 20, or equivalent device, through which externally-generated audio signals may be sensed.

As seen in FIG. 2, one of the unique features of the present disclosure is the use of two signal paths between the remote control unit 30 and the FIS 10, which two signal paths, in combination, provide a full-duplex communication channel between the remote control unit 30 and the FIS 10. A first signal path, represented in FIG. 2 by the wavy arrow 32, allows audio control signals, e.g., a sequence of audio tones, generated within the remote control unit 30 to be sent to the FIS 10. A second signal path, represented in FIG. 2 by the wavy arrow 34, allows back telemetry signals generated within the FIS 10 to be sent to the remote control unit 30. Advantageously, appropriate signals may be transmitted and received through the first and second signal paths up to a distance of 45–60 cm, or farther.

Figure 3:
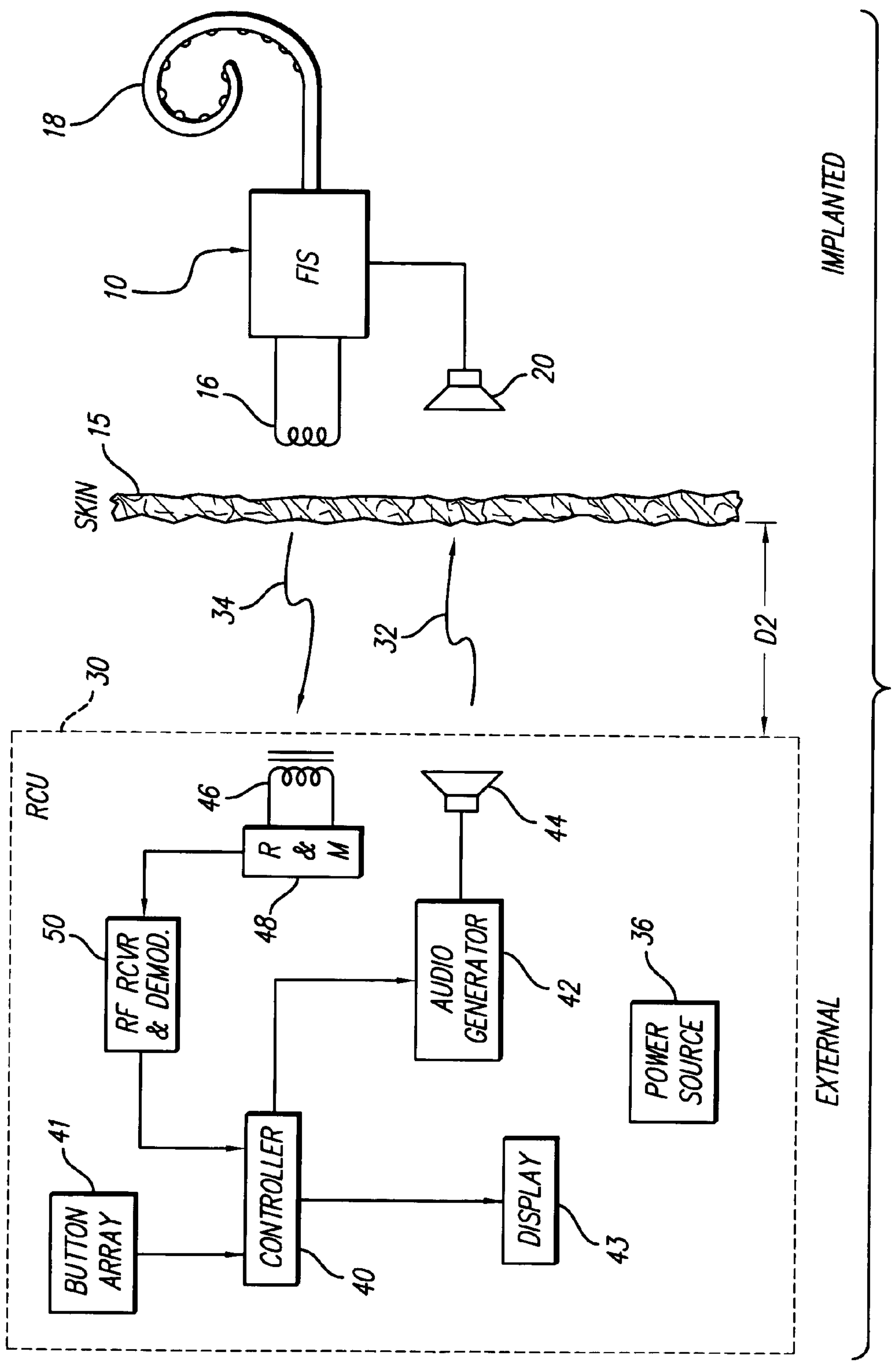
FIG. 3 shows a functional block diagram of the remote control unit of FIG. 2.

Turning next to FIG. 3, a functional block diagram of the remote control unit 30 is illustrated. It is to be emphasized that the block diagrams shown in FIG. 3 and the other figures presented herein, are functional in nature. Those of skill in the art may readily fashion numerous circuit configurations that achieve the circuit functions taught in these figures. The present disclosure is not intended to be limited by a particular circuit configuration.

As seen in FIG. 3, the remote control unit 30, in a preferred embodiment, includes a suitable power source 36, e.g., a replaceable battery, that provides operating power for the circuitry of the remote control unit. Controller circuitry 40, e.g., a suitable microprocessor or state-machine circuitry, generates appropriate control signals for sending to the FIS 10 in response to signals received through a button array 41 and/or back telemetry signals received from the FIS 10 and/or other signals (e.g., signals linked to the remote control unit from a clinician programming device). The control signals to be sent to the FIS 10 are sent to a tone generator circuit 42, which in turn drives a speaker 44 (or other suitable electrical-to-audio transducer). The speaker 44 generates audio tones as a function of the signals provided to it from the tone generator, and these audio tones are then coupled to the FIS over signal path 32, and are received by the microphone 20.

It is noted that while the microphone 20 is shown in FIG. 3 (and FIGS. 1 and 2) as being an implanted microphone, such is only exemplary. In practice, the microphone 20 may be any suitable device adapted to sense acoustic signals. Such microphone may be implanted or external. All that is required is that it be coupled in a suitable fashion with the FIS 10. For example, the microphone 20 could be placed inside the ear canal, as disclosed in the '474 patent, previously referenced; or the microphone could be located behind the ear, or clipped to an article of clothing, e.g., lapel or collar.

As further seen in FIG. 3, back telemetry signals generated by the FIS 10, and transmitted from the implanted coil 16, are received through signal path 34 by a rod antenna 46. A resonator and match circuit 48 is connected to the rod antenna 46 in order to help sense these signals (which are attenuated significantly by the relatively large distance D2 that the signals must travel). A suitable receiver 50, e.g., a BPSK receiver or an FM receiver, connected to the resonator and match circuit 48, extracts the informational portion (e.g., status data) from the received back telemetry signals and presents such data to the controller circuitry 40. A display 43, e.g., a flat screen LED (light emitting diode) display, or a combination of LED's or other visual indicators, may be used to provide an visual indication of the information received in the back telemetry signals received from the FIS 10. Such information may include an indication of whether the back telemetry signals have been properly received. Such indication may be in the form of a dynamic icon similar to what a conventional cell phone displays to indicate whether or not it is receiving a cell signal, i.e., whether it is within range to allow it to operate. Such information may also include an indication of the status of the FIS, e.g., the status of the power source within the FIS, the stimulation parameters currently associated with the FIS, and the like.

The ability of the remote control unit 30 to successfully receive a radio transmission from the FIS 10 is dependent upon the power and bandwidth of the transmission channel. Disadvantageously, the FIS 10 is not equipped to transmit a high power signal. Thus, the back telemetry signal, as it is typically called, is a relatively weak signal. For example, the back telemetry signal for a CLARION® implant device of the type disclosed in U.S. Pat. No. 5,603,726, incorporated herein by reference, which has a small multi-turn coil located inside of a ceramic implant package, is on the order of 100 μW to 1 mW (−10 to 0 dBm). The noise power in the receiver bandwidth of 500 KHz is −117 dBm. There is thus a margin of approximately 72 dB which could be used for propagation loss (separation of the transmitter and receiver), which propagation loss is quickly consumed as the separation distance increases.

In a FIS device of the type disclosed in the above-referenced '966 patent application, the situation is somewhat improved because the implant coil 16 has a larger diameter and resides external to the implant package. The implant coil 16 is designed primarily to be inductively coupled to an external coil 24 in a PSP/BTE headpiece 22 while the external coil and implant coil are in close proximity (0–8 mm) to each other (which PSP/BTE is typically used in the event of a battery failure or discharge condition). The implant coil 16 is also used to allow charging of a battery within the FIS, again using implant and external coils in close proximity (0–8 mm) to each other. Advantageously, the present disclosure also allows the implant coil 16 to function as an antenna during back telemetry transmission. (In contrast, prior art implant devices that have provided back telemetry capability, such as the CLARION device described in the '726 patent, have typically utilized a separate implanted coil within the implant device through which the back telemetry signal is transmitted.)

When transmitting a back telemetry signal, the receiving circuits in the remote control unit 30 must be configured in an appropriate manner in order to detect and receive the relatively weak back telemetry signal. The preferred back telemetry signal is a high frequency RF (radio frequency) signal, e.g., 10.7 MHz, modulated with binary phase-shift key (BPSK) information. Advantageously, BPSK is spectrally more efficient, and allows the use of a much simpler transmitter, than does a classical FM transmission. Variations of BPSK modulation may also be used, e.g., QPSK (quad phase-shift key). However, it is to be emphasized that in some instances, and for some applications, an FM signal centered at 10.7 MHz and having a bandwidth of about 500 KHz may also be used for the back-telemetry signal.

The preferred receiver configuration in the remote control unit, as shown in FIG. 3, uses a ferrite rod antenna 46, a resonator and match circuit 48 (to act as an impedance matching transformer to adjust the bandwidth and peak the signal response at 10.7 MHz), and an appropriate RF receiver and demodulation circuit 50 (which includes an RF amplifier having sufficient gain to amplify the received RF signal, and demodulation circuitry to demodulate the amplified RF signal and extract the BPSK or QPSK or FM information therefrom). With such configuration, sufficient sensitivity is obtained in the remote control receiver circuits to receive and demodulate the back telemetry signal at distances exceeding 24 inches (≈60 cm).

Numerous types of schemes may be used to implement the audio tone signals that are sent to the FIS 10 from the remote control unit 30. Any audio-tone generation scheme may be used with the present disclosure. A preferred scheme uses the acoustic signals to set or program the operating parameters, e.g., volume or sensitivity, speech processing strategy, and the like, of the implantable speech processor (ISP) included within the FIS 10.

As indicated, acoustic signals generated by the remote control unit provide the preferred approach for adjusting the operating parameters of the FIS. This is because the front-end receiving circuitry for sensing an acoustic signal, e.g., a microphone and audio pre-amplifier, is already present in the FIS, thus obviating the need for additional sensing/receiving circuitry and an additional receiving antenna coil to receive a remote control signal. That is, because space and power consumption are critical design parameters associated in the FIS 30, a design that avoids the use of additional components (such as a coil antenna, an RF receiving circuit, and the like) is highly advantageous. Moreover, an acoustic remote control unit offers the additional advantage of being able to be operated over a conventional telephone link without the need for any additional equipment. That is, in appropriate circumstances, a clinician or other medical personnel could send control signals to a user's FIS over the telephone by simply having the user place a telephone handset near the location where the FIS is implanted. Such over-a-telephone-line link would not allow full duplex operation (because the back telemetry signals would not be received over the telephone line), but it would afford one-way (half-duplex) communication with the FIS.

In a preferred operation, the controller 40 included within the remote control unit 30 causes the tone generator 42 to emit a n-bit burst command word, where n is an integer between about 4 and 32, modulated using frequency-shift-keying (FSK) of signals having frequencies f1 and f2. In one embodiment, the value of n is 32, and f1 is 1200 Hz and f2 is 2400 Hz. The bits of the command word are generated at a rate of between about 300 to 1200 bits per second. The receiver included within the FIS is a non-coherent receiver that discriminates between the f1/f2, e.g., 1200/2400 Hz, FSK signals using appropriate filters. Thus, a single bit of such command word would include either a signal at frequency f1 Hz, to signify a "0" or a signal at frequency f2 Hz, to signify a "1". The bits of the command word would have a duration determined by the bit rate, which bit rate lies within a range of between, e.g., 300 Hz (3.3 ms per bit) and 1200 Hz (0.83 ms per bit).

In one implementation, a single command word is emitted from the remote control unit 30 to, e.g., change the volume or sensitivity (i.e., to vary the amplitude of the stimulus pulses); select a desired speech processing strategy, place the FIS in a sleep or awake state; program the FIS; perform diagnostics; or alter some other operational parameter of the FIS. At the rates indicated (300 to 1200 bps), a single command word of 32 bits translates to a command duration ranging from about 26.7 ms (for a rate of 1200 bps) to about 106.7 ms (for a rate of 300 bps). Because the receiver in the FIS is a non-coherent receiver, the transfer rate is preferably selected to be closer to 300 bps rather than 1200 bps in order to allow more cycles of the f1/f2 FSK signal to occur during a bit period. Such brief, one-time-only, command word sent to the FIS 10 will not be perceived as anything more than a brief one-time "click" to the FIS user. Hence, this one-time "click" should not be an annoyance to the user. To the contrary, the one-time "click" advantageously provides reinforcing feedback to the user that a command signal has been received.

While the invention herein disclosed has been described by means of specific embodiments and applications thereof, numerous modifications and variations could be made thereto by those skilled in the art without departing from the scope of the invention set forth in the claims.

What is claimed is:

1. A method of controlling an implantable neural stimulator, the implantable neural stimulator having an implantable microphone for receiving externally-generated acoustic signals, and an implantable coil through which back telemetry signals may be transmitted, the method comprising:

establishing a full-duplex communications channel between the implantable neural stimulator and a remote control unit, wherein the full-duplex communications channel includes a first signal path through which command signals are sent to the implantable neural stimulator and a second signal path through with status signals are received from the implantable neural stimulator;

sending acoustic control signals through the first signal path, said acoustic control signals comprising the command signals; and receiving back telemetry signals through the second signal path, said back telemetry signals comprising the status signals.

2. The method of claim 1 wherein sending acoustic control signals comprises generating a n-bit burst command word, where n is an integer of between 4 and 32, and modulating the 32 bit burst command work using frequency-shift-keying (FSK) modulation.

3. The method of claim 2 wherein modulating the n-bit burst command word comprises applying FSK modulation to the n-bit burst command word that varies between frequency f1 Hz and frequency f2 Hz, at a rate of between approximately 300 to 1200 bits per second.

4. The method of claim 3 wherein f1 is 1200 Hz and f2 is 2400 Hz.

5. The method of claim 2 wherein sending acoustic control signals further comprises sending acoustic control signals to the implantable neural stimulator over a distance D2 cm, where the distance D2 is at least 45 cm and not greater than about 60 cm.

6. The method of claim 1 wherein receiving back telemetry signals comprises receiving a modulated RF carrier signal, wherein the RF carrier signal has a frequency of approximately 10.7 MHz, and wherein the RF carrier signal is modulated using modulation selected from BPSK, QPSK or FM.

7. The method of claim 6 wherein receiving back telemetry signals further comprises receiving signals from the implantable neural stimulator over a distance of D2 cm, where the distance D2 is at least about 45 cm and not greater than about 60 cm.

8. The method of claim 1 wherein the implantable neural stimulator includes an auditory fully implantable system.

9. The method of claim 8 wherein the auditory fully implantable system includes an implantable device capable of providing desired tissue or nerve stimulation.

10. The method of claim 9 wherein the auditory fully implantable system further includes stimulation parameters associated with the tissue stimulation provided by the implantable device.

11. The method of claim 10 wherein the implantable device includes an electrode array having a multiplicity of electrode contacts positionable to be in contact with body tissue that is to be stimulated.

12. The method of claim 1 wherein the remote control unit comprises an acoustic generator that generates acoustic control signals and an RF receiver circuit adapted to receive RF back telemetry signals generated by the implantable neural stimulator.

* * * * *